United States Patent [19]

Nolan

[11] 4,212,303
[45] Jul. 15, 1980

[54] UMBILICAL CORD CLAMP

[75] Inventor: John L. Nolan, Glenview, Ill.

[73] Assignee: Hollister Incorporated, Chicago, Ill.

[21] Appl. No.: 925,511

[22] Filed: Jul. 17, 1978

[51] Int. Cl.² ............................................. A61B 17/08
[52] U.S. Cl. .................................. 128/346; 24/248 B; 24/255 SL
[58] Field of Search ............................. 128/346, 325; 24/255 SL, 255 R, 237, 19, 270, 248 B; 251/10; D24/27

[56] References Cited

U.S. PATENT DOCUMENTS

| | | | |
|---|---|---|---|
| 2,947,055 | 8/1960 | McHenry | 24/237 X |
| 3,247,852 | 4/1966 | Schneider | 128/325 X |
| 3,854,482 | 12/1974 | Laugherty et al. | 128/346 |

FOREIGN PATENT DOCUMENTS 2525650  12/1976  Fed. Rep. of Germany ........... 128/346

Primary Examiner—William E. Kamm
Assistant Examiner—Michael H. Thaler
Attorney, Agent, or Firm—Tilton, Fallon, Lungmus & Chestnut

[57] ABSTRACT

An umbilical cord clamp having an improved lock construction. The clamp is of generally V-shaped configuration and includes a pair of flexible arms joined together at the apex of the V by an integral hinge. One of the arms is provided at its free forward end with a flexible tongue; the other arm has a forwardly-facing recess for receiving that tongue as the clamp is closed. A pair of projections extend inwardly from opposite sides of the recess and define sloping ramp surfaces for engaging the tip of the tongue and for flexing the tongue forwardly as the arms of the clamp are squeezed into closed condition. When the clamp is fully closed, the tip of the tongue snaps into position beneath the undercut projections to lock the arms securely together.

14 Claims, 7 Drawing Figures

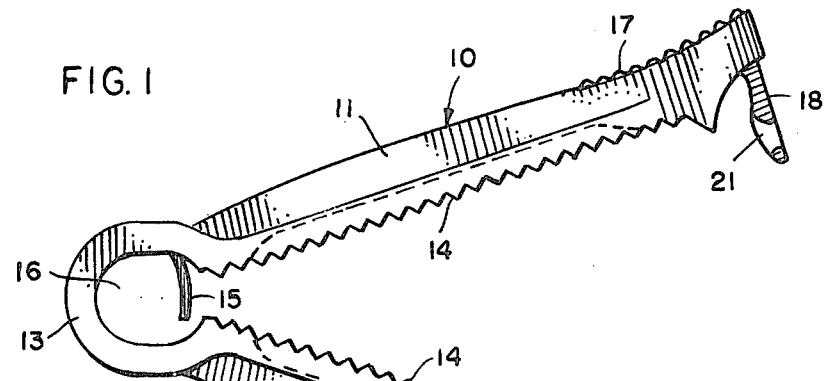
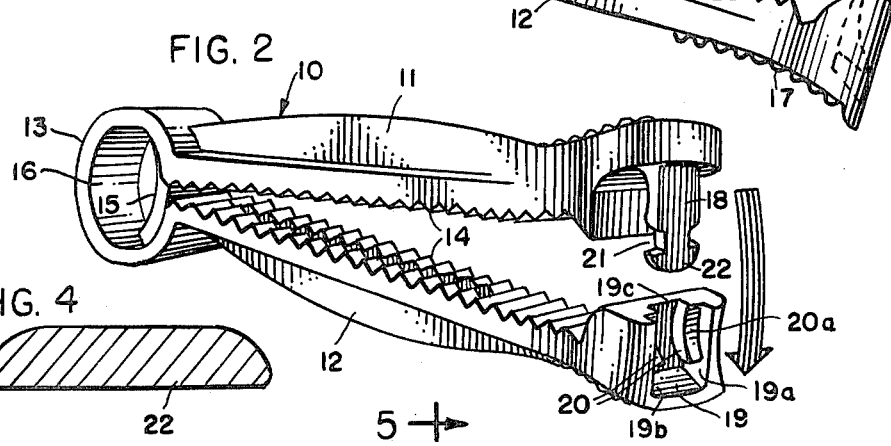
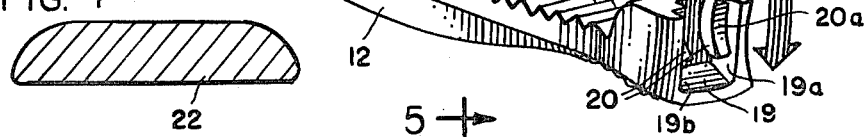
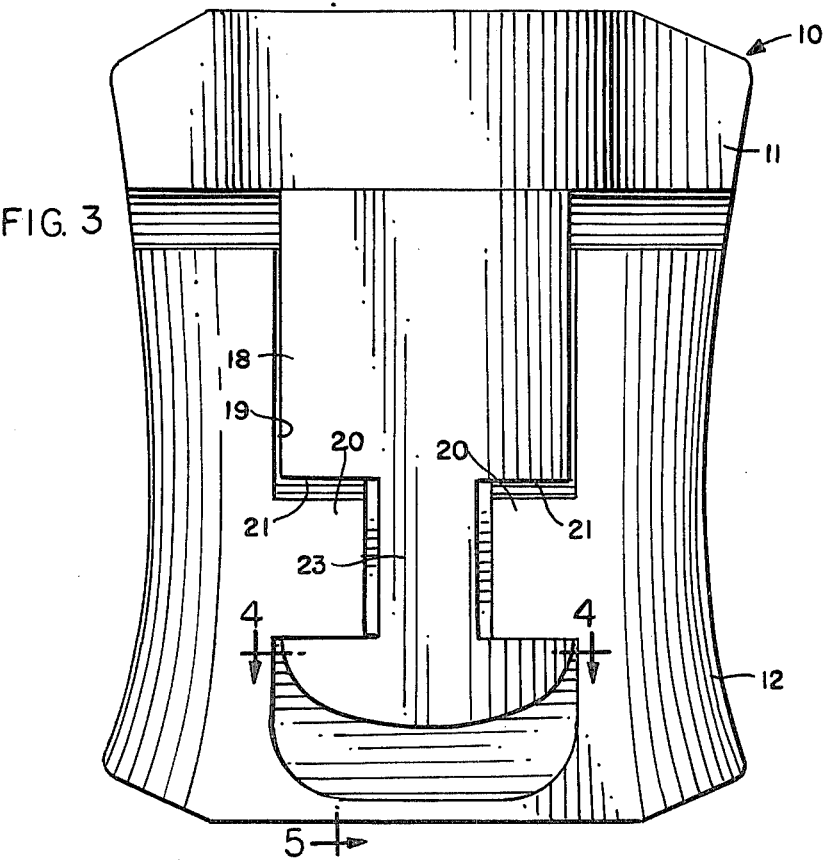

UMBILICAL CORD CLAMP

BACKGROUND AND SUMMARY

Co-owned U.S. Pat. No. 3,247,852 discloses an inexpensive, disposable, and widely used umbilical cord clamp for closing the umbilical cord of a newborn infant. The clamp is formed of flexible plastic, has a pair of arms joined by an integral hinge, and is provided with locking means in the form of a hook portion 16 receivable in a recess 18 when the clamp is closed (FIG. 2).

Despite the effectiveness of the clamp disclosed in the aforementioned patent, the device lacks visual means for clearly indicating to a user that complete latching or locking has occurred. FIG. 2 of the patent depicts hook 16 as being fully inserted in recess 18. While that is the fully latched condition of the hook when the clamp is closed, the fact remains that a user, without the benefit of the sectional view of FIG. 2, looking only at the outer surfaces of the closed clamp, could not easily determine with certainty that the hook is fully received within the recess instead of being only partially received within that recess.

It is therefore an object of this invention to provide an umbilical cord clamp equipped with a lock construction that provides a clear visual (also audible) indication to a user tha the parts are completely locked together. In addition, it is an object to provide a clamp having arms which lock together even more securely under conditions which distort the arms, that is, under conditions which cause an outward bowing of the arms by reason of the cord clamped therebetween. A particularly important aspect of the invention lies in providing a latching or locking mechanism which provides exceptional security without requiring increased closing force for its operation. The force required to close a clamp embodying this invention is in fact reduced without any sacrifice in security and with the advantages of clear visual and audible indications of latch operation.

Briefly stated, the clamp is of generally V-shaped configuration and has a pair of flexible arms with rear end portions joined together by an integral hinge at the apex of the V-shaped clamp. The free forward ends of the arms are normally disposed in spaced relation and are movable towards each other for the purpose of clamping an umbilical cord between the arms. The locking means for securing the arms together takes the form of a flexible tongue at the forward end of one of the arms, the tongue projecting towards the other arm in the direction of locking movement of the first arm. The other arm, or second arm, has a forwardly-facing recess at its free end for receiving the tongue. A pair of projections extend into the recess from opposite sides thereof, such projections having forwardly-sloping ramp surfaces which are engagable with the tip of the tongue for flexing that tongue forwardly as the clamp is squeezed into partially closed condition. The tongue has a pair of lateral notches which are spaced from the tip for receiving the projections after the tongue has cleared the ramp surfaces and has snapped rearwardly into an unflexed and untensioned locking condition. With the tongue in that condition, the side projections are clearly visible, and preferably protrude slightly forwardly through, the lateral notches of the tongue to provide a clear visual indication that the arms are fully locked together.

As the elongated tongue snaps into its locking position, it engages the other arm with a forceful snap or click, thereby giving an audible signal that locking or latching has occurred. Further security is achieved by reason of the fact that outward bowing of the arms tends to force the latched tongue rearwardly into even greater latching engagement with the lateral projections. In the preferred embodiment disclosed herein, a slight spacing may be provided between the rear surface of the recess and the tongue when the clamp is closed without appreciable bowing of the arms, such space thereby accommodating limited additional rearward displacement of the tip portion of the tongue when the clamp is closed under conditions which cause substantial outward bowing of such arms. Under extreme conditions, as where arm distortion is so great that the tongue is forced to bend in its latched or locked condition, such bending action enhances rather than reduces the security of the interlocking relationship.

Other features, advantages, and objects of the invention will become apparent from the specification and drawings. For a more complete understanding of the state of the prior art, reference may be had to U.S. Pat. Nos. 3,854,482, 3,735,765, and 3,822,052.

DRAWINGS

FIG. 1 is a side elevational view of an umbilical cord clamp embodying the invention, the clamp being shown in open condition.

FIG. 2 is a perspective view showing the clamp after its arms have been urged towards each other into a partially closed condition.

FIG. 3 is a greatly enlarged front elevational view showing the clamp in closed condition.

FIG. 4 is a sectional view of the tongue taken along line 4—4 of FIG. 3.

DETAILED DESCRIPTION

Figure 6:
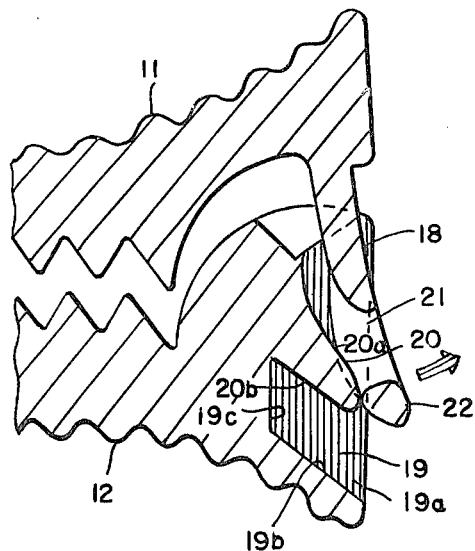
FIG. 6 is a vertical sectional view similar to FIG. 5 but showing the clamp as its arms are being closed and as the tongue is flexed forwardly to clear the side projections within the recess of the lower arm.

Referring to the drawings, the numeral 10 generally designates an umbilical cord clamp having arms 11 and 12 joined at their rear ends by an integral hinge 13. The clamp as shown is formed from a single piece of resilient, flexible material, preferably one which can be autoclaved before use. Nylon has been found to be suitable for this purpose, but other plastic materials having similar properties of flexibility, durability and autoclavability may be used.

The opposing surfaces of the arms are provided with teeth 14 to help provide a secure grip on an umbilical cord clamped therebetween. To prevent a cord from entering the opening within enlarged loop hinge 13, a blocking element 15 is formed integrally with one of the arms and closes off the entrance to the opening 16 when the clamp is in the open position shown in FIG. 1. It is believed apparent that the blocking member 15, which flexes upon engagement with the other arm as the clamp is closed, continues to perform its blocking function throughout the closing operation.

Near their free forward ends, arms 11 and 12 are provided with transverse ribs 17 along their outwardly-facing surfaces to facilitate the secure gripping and manipulating of the clamp in use. It is to be understood that in referring to arms 11 and 12, terms such as "forwardly", "rearwardly", "upper", and "lower" are sometimes used herein to aid in the description of the drawings and to assist in relating the parts to each other, but that such terms are not intended to suggest any particular orientation of the clamp when it is used.

The structure as so far described is well known and is disclosed in U.S. Pat. No. 3,247,852. The features of this invention relate primarily to the means for locking the clamp in closed condition, and to the unique cooperative relationships which arise when such locking means operates in conjunction with the remaining parts of the clamp taken as a whole.

The locking means is located at the free forward ends of the arms and includes a flexible tongue 18 formed integrally with upper arm 11 and extending generally towards lower arm 12. The lower arm is provided with a forwardly-facing recess 19 for receiving the tongue as the clamp is closed (FIG. 2). The recess is defined by generally parallel side surfaces 19a and by bottom and rear surfaces 19b and 19c, respectively. Within the recess, extending inwardly from opposite side surfaces 19a, are a pair of spaced projections 20. As shown most clearly in FIGS. 2 and 6-7, the spaced parallel projections are disposed above bottom surface 19 and are provided with downwardly and forwardly sloping ramp surfaces 20a, such ramp surfaces being adapted for camming engagement with the tip of tongue 18 in the manner hereinafter described. It will also be noted that the projections 20 are undercut; that is, they are provided with undersurfaces 20b which slope upwardly and rearwardly as indicated in FIG. 6.

Figure 5:
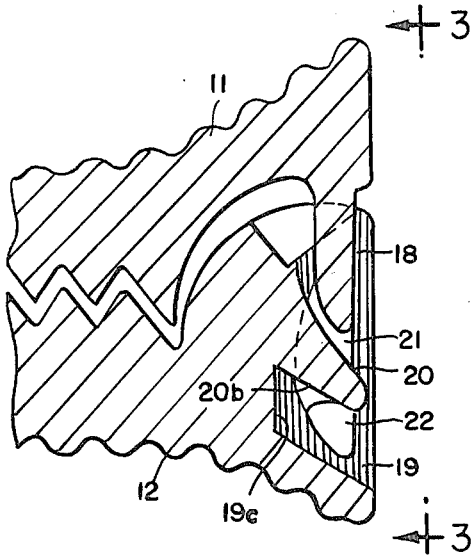
FIG. 5 is a fragmentary sectional view taken along line 5—5 of FIG. 3 but in reduced scale, showing the relationship of parts when the clamp is in closed condition.

The elongated tongue 18 is provided with a pair of lateral notches 21 which receive projections 20 when the clamp is fully closed (FIGS. 3 and 5). Under such conditions, the tip portion 22 of the tongue is disposed within the recess beneath projections 20.

Referring to FIG. 5, it will be seen that the tongue 18 is spaced slightly in front of the rear surface 19c of the recess when the clamp is in closed condition without significant distortion of arms 11 and 12. Should forces be exerted that would tend to urge the free ends of the arms apart, such forces would have the effect of causing tip 22 to ride upwardly and rearwardly along the sloping surfaces 20b of the undercut projections 20, thereby causing the tongue to latch even more securely to the projections. Deformation of the projections 20 in response to such forces is resisted because the projections are inward extensions of side surfaces 19a and, hence, are not free to flex or bend upwardly to any appreciable extent.

An important aspect of the lock construction and its operation lies in the fact that stresses arising when a cord is clamped between the arms extend primarily in a direction running longitudinally of the elongated tongue. Because such stresses are in-line rather than offset with respect to the tongue, the reaction forces which are exerted by the clamped cord and which urge the free ends of the arms away from each other do not have the effect of causing the tip of the tongue to bend or tip forwardly away from the projections. As indicated, just the opposite effect takes place. In-line stresses of tongue 18, coupled with the camming effect produced by the sloping undersurfaces 20b engaged by tip 22, cause the tongue to flex rearwardly and to move tip 22 even more deeply into recess 19. In terms of function, the tongue might be considered as having a pair of lateral hook portions, specifically, the two oppositely-directed portions of tip 22 disposed directly beneath notches 21. Since those hook portions do not projects either forwardly or rearwardly with respect to the tongue, downward forces applied to those hook portions would not have a tendency to bend the tongue either forwardly or rearwardly. That the tongue does flex rearwardly as reaction forces increase results from the fact that the forces imposed on the hook portions are not directed precisely downwardly but are instead angled rearwardly because of the slope of surfaces 20b. Furthermore, while a strong downward force on each hook portion might have the effect of causing that portion to bend slightly downwardly, it cannot shift laterally out of locking engagement with projection 20 because the width of recess 19 does not permit any appreciable lateral displacement of the tongue and because any such forces tending to cause lateral displacement in one direction are offset by similar forces exerted on the other hook portion tending to displace the tongue in the opposite lateral direction.

Figure 7:
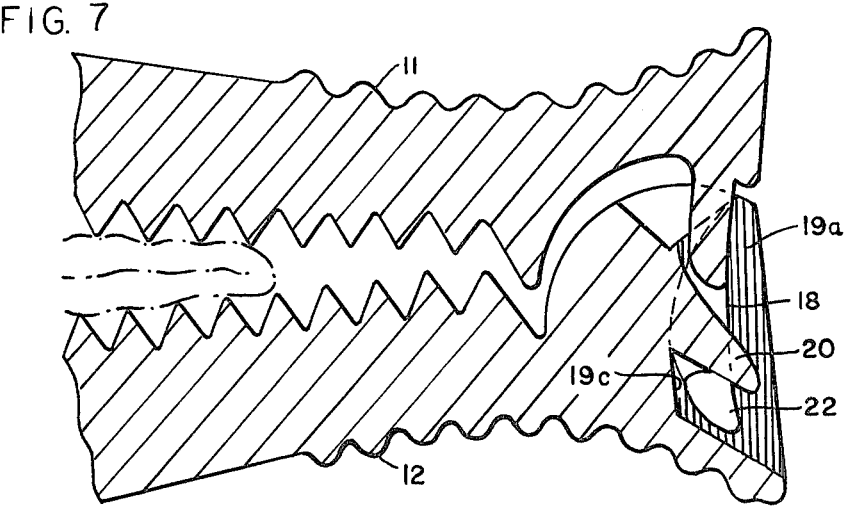
FIG. 7 is a vertical sectional view similar to FIGS. 5 and 6 but illustrating the relationship of parts when the clamp is fully closed upon an umbilical cord, the view being somewhat exaggerated to illustrate an extreme condition of use.

Under extreme conditions, as where a cord clamped between arms 11 and 12 causes substantial bowing of those arms, a canting or tipping action occurs at the free ends of the arms which forces tongue 18 into firm engagement with rear wall 19c of the recess, even to the extent of producing limited flexure of tongue 18 (FIG. 7). The force exerted by the tongue as it resists such bending simply increases the force which holds the tongue in locking engagement with projections 20. The result is a lock construction which is well suited to resist yielding to the forces tending to cause separation of the arms even under extreme conditions of use.

As depicted in FIG. 3, the leading surfaces of projections 20 remain clearly visible from the front end of the clamp even when the clamp is fully closed. Visual verification that the clamp is indeed in fully locked condition is achieved simply by viewing projections 20 through notches 21 of the tongue. Such a visual check may be augmented by tactile verification since, as shown in FIGS. 5 and 7, projections 20 extend forwardly beyond tongue 18 when the arms are locked together.

FIGS. 5-7 reveal that the front-to-rear thickness of the tongue 18 is greatest along that portion which bridges notches 21; that is, the stem portion 23 of the tongue (FIG. 3) is thicker than those portions above and below it to strengthen the tongue and compensate for the absence of material occasioned by notches 21. Preferably, the increased dimension is achieved by smoothly contouring the tongue to define an arcuate rear surface as viewed from the side (FIGS. 1 and 5-7). Also, to promote smooth latching or locking operation, the undersurface of tip 22 may be curved as viewed in front elevation (FIG. 3) and the rear edges of the tip may be rounded as viewed in transverse section (FIG. 4). The result is a tongue having a tip 22 which slides easily and smoothly upon sloping ramp surfaces 20a of projections 20 as the arms 11, 12 are urged towards each other. As the clamp is closed, the camming engagement between tip 22 and surface 20a causes the elongated tongue to flex forwardly (FIG. 6). Finally, as the tip clears projections 20, the tongue snaps rearwardly to swing the tip into that portion of the recess beneath the projections. Engagement between the tongue and surfaces 19b and 19c, as the tongue snaps into the recess and momentarily contacts such surfaces, produces a sharp click which provides an audible signal that the clamp is locked in closed condition.

As already indicated, tongue 18 may be regarded as having a pair of lateral hook portions, in contrast to earlier constructions provided with rearwardly-projecting hook portions. Because of such lateral hook portions, tongue 18 need not flex as far forwardly to clear projections 20 as might otherwise be required if it had one or more rearwardly-projecting hook portions. Consequently, the lateral hook construction, augmented by the rounded surfaces and substantial length of the tongue, result in a clamp which requires a relatively low closing force.

While in the foregoing an embodiment of the invention has been disclosed in considerable detail for purposes of illustration, it will be understood by those skilled in the art that many of these details may be varied without departing from the spirit and scope of the invention.

I claim:

1. An umbilical cord clamp of generally V-shaped configuration comprising a pair of flexible arms having rear end portions joined together by an integral hinge at the apex of the V and having free forward end portions normally disposed in spaced-apart relation and being movable towards each other for clamping an umbilical cord between said arms, and locking means for securing said arms together when said clamp is closed, wherein the improvement comprises said locking means includes a flexible tongue at the forward end of one of said arms, said tongue projecting towards the other of said arms in the general direction of closing movement of said one arm, said other arm having a recess at its forward end for receiving said tongue and having a pair of transversely-spaced projections extending into said recess from opposite sides thereof, said tongue having a tip portion and said projections defining a pair of forwardly sloping ramp surfaces engagable with said tip portion for flexing the tongue forwardly as said arms are urged together, said tongue having a pair of lateral notches adjacent said tip portion for receiving said pair of projections when said tip portion has cleared said ramp surfaces and said clamp is fully closed.

2. The clamp of claim 1 in which said notches extend completely through said tongue to expose said projections from the front of said clamp when said arms are locked in closed condition.

3. The clamp of claim 1 in which said projections of said other arm have undersurfaces which slope fowardly and away from said one arm.

4. The clamp of claim 1 in which said projections extend forwardly a distance greater than the thickness of said tongue, said projections extending forwardly through said notches beyond said tongue when said clamp is closed.

5. The clamp of claim 1 in which said tip portion has a lower margin of arcuate configuration.

6. The clamp of claim 1 in which said tip portion has rounded rear edges when viewed in transverse section.

7. The clamp of claim 1 in which said recess opens forwardly and has a width only slightly greater than the width of said tongue, the sides of said recess being slidably engagable with said tongue for guiding the same into locking position as said clamp is closed.

8. The clamp of claim 1 in which said recess is defined in part by a rear surface spaced behind said tongue when said clamp is in fully closed condition with said arms substantially unflexed.

9. An umbilical cord clamp of generally V-shaped configuration formed of flexible plastic material, said clamp having a pair of arms with rear end portions joined together by an integral hinge at the apex of the V and having free forward end portions normally disposed in spaced-apart relation and being movable towards each other for clamping an umbilical cord between said arms, and locking means for securing said arms together when said clamp is closed, wherein the improvement comprises said locking means includes a flexible tongue at the forward end of one of said arms, said tongue projecting towards the other of said arms in the general direction of closing movement of said one arm and having a tip providing a pair of lateral hook portions, said other arm having a recess at its forward end for receiving said tongue, said recess being defined by a pair of transversely-spaced opposing side surfaces and a rear surface and being open towards the front of said other arm, said other arm also having a pair of transversely-spaced projections extending into said recess from said opposing side surfaces and defining a pair of forwardly sloping ramp surfaces for engaging said hook portions of said tongue to flex said tongue forwardly as said arms are urged together, said tongue having a pair of lateral notches adjacent to said hook portions for receiving said pair of projections, said hook portions being disposed beneath said notches for engaging the undersides of said projections when said clamp is fully closed.

10. The clamp of claim 9 in which said notches extend completely through said tongue to expose said projections from the front of said clamp when said arms are locked in closed condition.

11. The clamp of claim 9 in which said projections have undersurfaces which slope forwardly and downwardly, whereby, said sloping undersurfaces engage said hook portions to urge said tip of said tongue more deeply into said recess in response to forces tending to urge said arms apart when said clamp is fully closed.

12. The clamp of claim 11 in which said rear surface of said recess is spaced a substantial distance behind said tongue when said clamp is in fully closed condition with said arms substantially unflexed.

13. The clamp of claim 9 in which said projections extend forwardly a distance greater than the thickness of said tongue, said projections extending forwardly through said notches beyond said tongue when said clamp is fully closed.

14. The clamp of claim 9 in which said side surfaces of said recess are spaced apart a distance only slightly greater than the width of said tongue and are slidably engagable with said tongue for guiding the same into locking position as said clamp is closed.

* * * * *